United States Patent
Kwak et al.

(10) Patent No.: US 10,345,223 B2
(45) Date of Patent: Jul. 9, 2019

(54) OPTICAL GAS SENSOR

(71) Applicant: SAMSUNG ELECTRONICS CO., LTD., Suwon-si (KR)

(72) Inventors: Hyun-suk Kwak, Seoul (KR); Kwang-bok Kim, Incheon (KR); Dae-kwang Jung, Suwon-si (KR); Yong-won Jeong, Seoul (KR); Jun-ho Koh, Suwon-si (KR); Chang-hyun Kim, Seoul (KR); Yong-chan Lee, Seoul (KR); Jeong-eun Lee, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 16/063,164

(22) PCT Filed: Sep. 12, 2016

(86) PCT No.: PCT/KR2016/010246
§ 371 (c)(1),
(2) Date: Jun. 15, 2018

(87) PCT Pub. No.: WO2017/104940
PCT Pub. Date: Jun. 22, 2017

(65) Prior Publication Data
US 2018/0372618 A1  Dec. 27, 2018

(30) Foreign Application Priority Data

Dec. 16, 2015 (KR) .......... 10-2015-0180144

(51) Int. Cl.
*G02B 6/02* (2006.01)
*G01N 21/03* (2006.01)
(Continued)

(52) U.S. Cl.
CPC ............ *G01N 21/05* (2013.01); *G01N 21/03* (2013.01); *G01N 21/31* (2013.01); *G01N 33/497* (2013.01); *G02B 6/02* (2013.01)

(58) Field of Classification Search
CPC ...... G01N 21/05; G01N 21/31; G01N 33/497; G02B 6/122
See application file for complete search history.

(56) References Cited

U.S. PATENT DOCUMENTS

| 5,341,214 A | 8/1994 | Wong |
| 5,488,227 A | 1/1996 | Sweet |

(Continued)

FOREIGN PATENT DOCUMENTS

| JP | 2013-250193 A | 12/2013 |
| KR | 10-2006-0127447 A | 12/2006 |

(Continued)

OTHER PUBLICATIONS

Search Report dated Dec. 16, 2016, issued by the International Searching Authority in counterpart International Patent Application No. PCT/KR2016/010246 (PCT/ISA/210).

*Primary Examiner* — Maurice C Smith
(74) *Attorney, Agent, or Firm* — Sughrue Mion, PLLC

(57) ABSTRACT

Disclosed is an optical gas sensor. The optical gas sensor includes: a light source which emits light; a gas collector which includes a cavity to be filled with gas to be sensed; an optical wave guider which guides light emitted from the light source to be output to the cavity, and guides the output light to be output again to the cavity after passing through the cavity of the gas collector; and an optical detector which detects light output from the optical wave guider. Thus, a path of light exposed to the gas to be sensed is increased within the cavity, thereby achieving miniaturization and sensing gas of low-concentration.

18 Claims, 17 Drawing Sheets

(51) Int. Cl.
  *G01N 21/05* (2006.01)
  *G01N 21/31* (2006.01)
  *G01N 33/497* (2006.01)

(56) References Cited

U.S. PATENT DOCUMENTS

| | | | |
|---|---|---|---|
| 2009/0175578 A1* | 7/2009 | Strabley | G01C 19/727 |
| | | | 385/39 |
| 2011/0299076 A1* | 12/2011 | Feitisch | G01J 3/28 |
| | | | 356/326 |
| 2012/0300198 A1* | 11/2012 | Wu | H01S 5/06258 |
| | | | 356/149 |
| 2013/0003045 A1 | 1/2013 | Wilkins | |
| 2013/0081447 A1 | 4/2013 | Carter et al. | |
| 2014/0205285 A1* | 7/2014 | Jiang | H04Q 1/00 |
| | | | 398/45 |
| 2016/0069797 A1* | 3/2016 | Chanda | G01N 21/39 |
| | | | 356/437 |

FOREIGN PATENT DOCUMENTS

| | | |
|---|---|---|
| KR | 10-0782352 B1 | 12/2007 |
| KR | 10-2009-0105757 A | 10/2009 |
| KR | 10-1105687 B1 | 1/2012 |
| KR | 10-2014-0076973 A | 6/2014 |

* cited by examiner

OPTICAL GAS SENSOR

TECHNICAL FIELD

The present invention relates to an optical gas sensor.

BACKGROUND ART

A medical examination performed in a hospital needs to collect blood or tissue from chronic illness patients and thus has disadvantages of putting the patients to a lot of inconvenience. Recently, there have been continued researches on a noninvasive method of diagnosing diseases, for example, chronic obstructive pulmonary disease (COPD), asthma, pulmonary tuberculosis, lung cancer, diabetes, etc. based on a human-body respiratory gas analysis.

An optical gas sensor has been employed in analyzing a spectrum and diagnosing chronic diseases on the principle that various respiratory gases, for example, nitrogen monoxide (NO), carbon monoxide (CO), acetone or the like gas which reflects a human body's physical conditions are different in wavelength of light absorbed therein while transmitting the light.

There has been disclosed an optical gas sensor (US 2013/0081447), in which a hollow optical waveguide having a diameter of about 2 mm is manufactured as folded or twisted to get a long optical path within a small space, and components of gas are detected by transmitting light through the optical waveguide internally filled with the gas to be sensed.

Such a conventional optical gas sensor additionally needs a pump for inhaling and exhausting the respiratory gas in a small and complicated optical waveguide, and thus has a limit to miniaturization and a complicated structure.

DISCLOSURE

Technical Problem

The present invention is conceived to solve the conventional problems, and an object of the present invention is to provide an optical gas sensor that can have a small and simple structure.

Another object of the present invention is to accurately sense gas having a low concentration since it is possible to increase an optical path within a small structure.

Technical Solution

There is provided an optical gas sensor to solve the technical problem of the present invention. The optical gas sensor including: a light source which emits light; a gas collector which includes a cavity to be filled with gas to be sensed; an optical wave guider which guides light emitted from the light source to be output to the cavity, and guides the output light to be output again to the cavity after passing through the cavity of the gas collector; and an optical detector which detects light output from the optical wave guider.

Thus, it is possible to miniaturize the optical gas sensor while effectively increasing an optical path.

The optical wave guider includes: an optical inlet which includes an entrance to which light emitted from the light source is input, and an exit from which the light input through the entrance is output to the cavity; at least one optical bypass by which light passed through the cavity is bypassed to be output again to the cavity; and an optical outlet which outputs light passed through the optical bypass to an outside.

The gas collector may be shaped like a barrel opened up and down.

The gas collector may be shaped like one of a cylinder and a rectangular box.

The optical wave guider may be formed on face-to-face surfaces of two or more substrates.

The optical wave guider may be formed on one surface of face-to-face surfaces of two or more substrates.

The gas collector may include two substrates, and the optical inlet and the optical bypass may be formed in one substrate and the optical outlet may be formed in the other adjacent substrate.

The gas collector may include three substrates, and the optical wave guider may be formed in a middle substrate among the three substrates.

The gas collector may include three or more substrates, and the optical inlet, the optical bypass and the optical outlet may be dispersedly formed throughout the three or more substrates.

The optical wave guider may have a cross section shaped like one of a quadrangle, a trapezoid, a hexagon, a triangle, a semicircle, a circle, a diamond and an octagon.

At least one of an optical entrance for an input to the cavity and an optical exit for an output from the cavity may be shaped like a funnel.

The optical exit may include a collimating lens.

The optical exit may include a condensing lens.

A distance between an optical entrance for an input to the cavity and an optical exit for an output from the cavity may be adjustable.

The quantity of light emitted from the light source may be varied depending on adjustment of the distance.

Advantageous Effects

As described above, according to the present invention, it is possible to miniaturize an optical gas sensor even while increasing an optical path, and accurately sense gas having a low concentration.

BEST MODE

Figure 1:
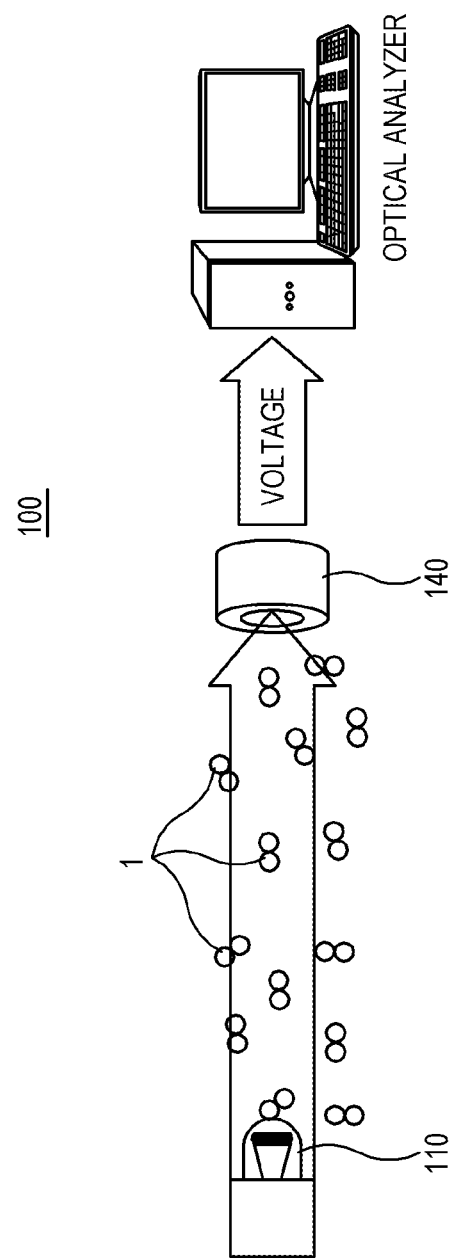
FIG. 1 illustrates a principle of an optical gas sensor.

Below, embodiments of the present invention will be described with reference to accompanying drawings. The following embodiments have to be considered as illustrative only, and it should be construed that all suitable modification, equivalents and/or alternatives fall within the scope of the invention. Throughout the drawings, like numerals refer to like elements.

In this specification, "have," "may have," "include," "may include" or the like expression refer to presence of the corresponding features (e.g.: numerical values, functions, operations, or elements of parts, and does not exclude additional features.

In this specification, "A or B," "at least one of A or/and B," "one or more of A or/and B" or the like expression may involve any possible combination of listed elements. For example, "A or B," "at least one of A and B," or "at least one A or B" may refer all of (1) at least one A, (2) at least one B, or (3) both at least one A and at least one B.

In this specification, "a first," "a second," "the first," "the second" or the like expression may modify various elements regardless of order and/or importance, and does not limit the elements. These expressions may be used to distinguish one element from another element. For example, a first user device and a second user device are irrelevant to order or importance, and may be used to express different user devices. For example, a first element may be named a second element and vice versa without departing from the scope of the invention.

If a certain element (e.g. the first element) is "operatively or communicatively coupled with/to" or "connected to" a different element (e.g. second element), it will be understood that the certain element is directly coupled to the different element or coupled to the different element via another element (e.g. third element). On the other hand, if a certain element (e.g. the first element) is "directly coupled to" or "directly connected to" the different element (e. g. the second element), it will be understood that another element (e.g. the third element) is not interposed between the certain element and the different element.

In this specification, the expression of "configured to" may be for example replaced by "suitable for," "having the capacity to," "designed to," "adapted to," "made to," or "capable of" in accordance with circumstances. The expression of "configured to" may not necessarily refer to only "specifically designed to" in terms of hardware. Instead, the "device configured to" may refer to "capable of" together with other devices or parts in a certain circumstance. For example, the phrase of "the processor configured to perform A, B, and C" may refer to a dedicated processor (e.g. an embedded processor) for performing the corresponding operations, or a generic-purpose processor (e.g. a central processing unit (CPU) or an application processor) for performing the corresponding operations by executing one or more software programs stored in a memory device.

In this specification, terms may be used just for explaining a certain embodiment and not intended to limit the scope of other embodiments. A singular expression may involve a plural expression as long as it does not clearly give different meaning contextually. All the terms set forth herein, including technical or scientific terms, have the same meanings as those generally understood by a person having an ordinary skill in the art. Terms defined in a general-purpose dictionary may be construed to have the same or similar meanings as the contextual meanings of the related art, and should not be interpreted as ideally or excessively formal meanings. As necessary, even the terms defined in this specification may be not construed to exclude the embodiments of the present invention.

Figure 2:
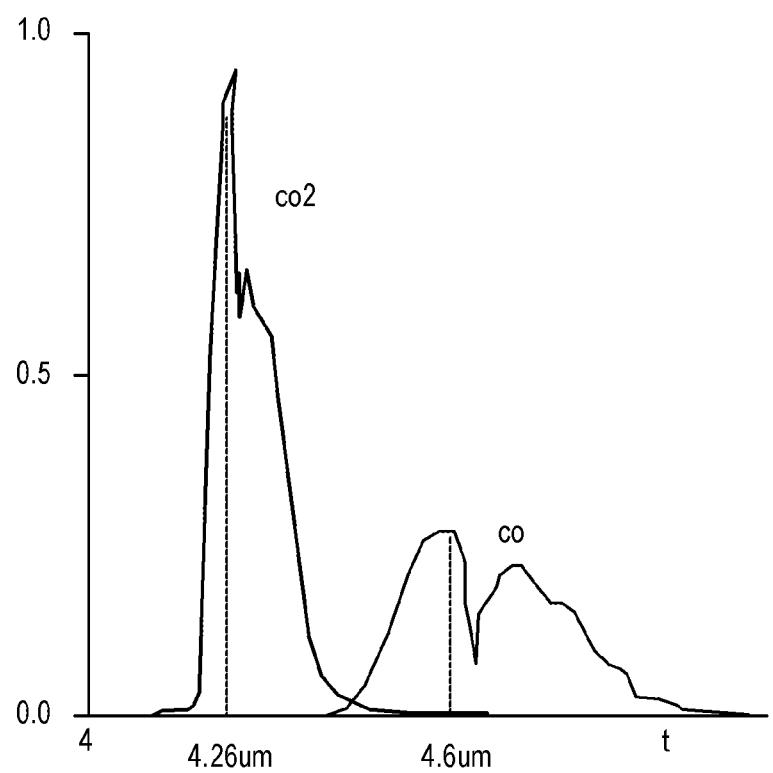
FIG. 2 is a graph of showing gas components resulting from an analysis of light detected in the optical gas sensor.

FIG. 1 is a perspective view of a gas sensing principle of an optical gas sensor 100. Light emitted from a light source 110 passes through a gas chamber and is then detected in an optical detector 140. Gas molecules 1 absorb light of specific wavelengths according to the kinds of gas. Therefore, it is possible to determine the kind of gas by detecting light passed through the gas and analyzing the wavelengths by a spectroscope. FIG. 2 is a graph resulting from detecting and analyzing light passed through a gas, in which carbon dioxide ($CO_2$) absorbs light having a wavelength of 4.26 μm, and carbon monoxide (CO) absorbs light having a wavelength of 4.6 μm.

Differential optical absorption spectroscopy (DOAS) uses the Beer-Lambert's law of establishing the following Expression 1.

$$I=I_o \times 10^{-\varepsilon cl} \qquad \text{[Expression 1]}$$

where, I is intensity of transmitted light, $I_o$ is intensity of incident light, c is concentration, l is a length of an optical path, and ε is a light absorption coefficient.

According to the Beer-Lambert's law, an optical path has to become longer in order to not only more improve accuracy in gas detection but also more easily achieve the gas detection even under low concentration. However, the longer the optical path is, the bigger a gas sensing device is. Therefore, when the gas sensing device is designed to be portable, there is a need of reducing the size of the gas sensing device while making the optical path longer.

Figure 3:
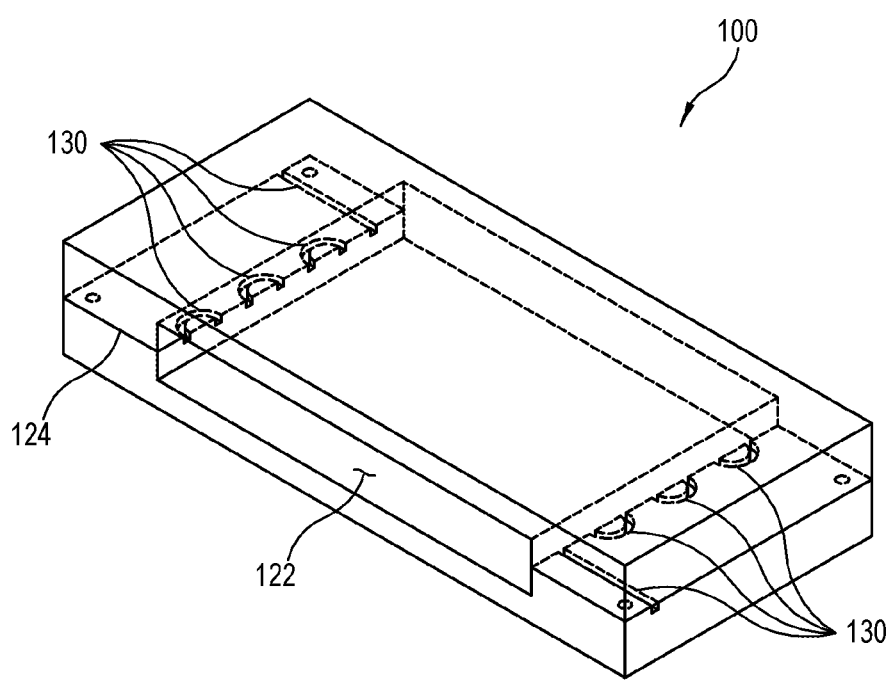
FIG. 3 is a perspective view of an optical gas sensor according to a first embodiment of the present invention.
Figure 4:
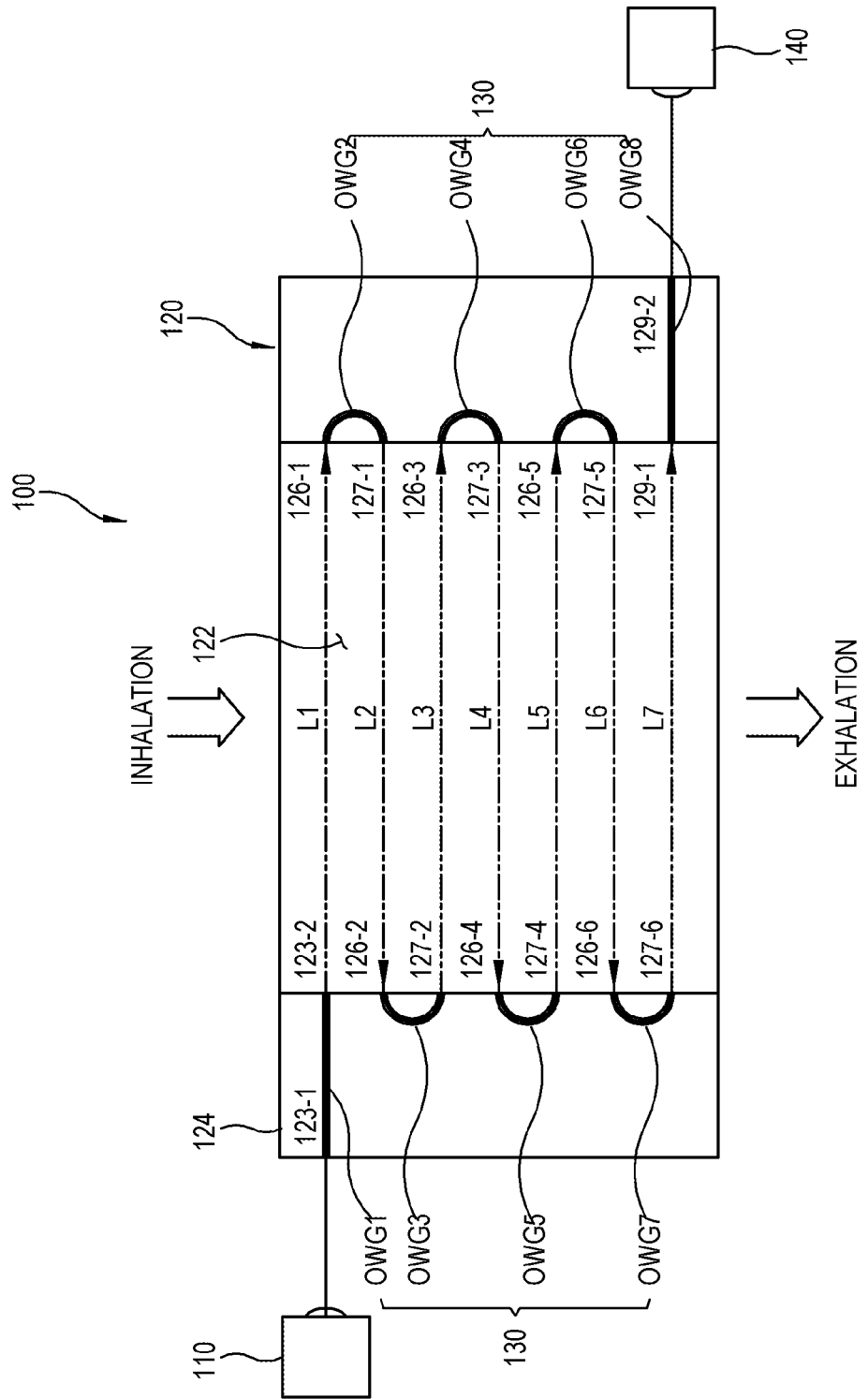
FIG. 4 is a cross-section view of the optical gas sensor of FIG. 1.

FIGS. 3 and 4 are a perspective view and a cross-section view of an optical gas sensor 100 according to a first embodiment of the present invention, respectively. The optical gas sensor 100 includes a light source 110 for emitting light, a gas collector 120 having a cavity 122 opened up and down in a middle thereof for collecting gas to be sensed, an optical wave guider 130 formed in a wall 124 of the gas collector 120, and an optical detector 140 for detecting light finally output from the optical wave guider 130.

The light source 110 is materialized by one among a light emitting diode (LED), a xenon lamp, a metal halide lamp, a halogen lamp, a tungsten lamp, a ceramic metal lamp, a high-pressure sodium lamp, a fluorescent lamp, and sunlight.

The gas to be sensed includes one among carbon monoxide, carbon dioxide, ozone, sulfurous acid gas, nitrogen oxide, ammonia, hydrogen peroxide, volatile organic compounds (VOCs) (e.g. formaldehyde, acetone, isoprene, benzene, toluene, etc.), and volatile sulfide compounds (VSCs) (hydrogen sulfide, methyl mercaptan).

The gas collector 120 may be made of poly carbonate, Teflon, aluminum alloy, etc. The gas collector 120 may be manufactured as a barrel type, for example, a rectangular box or a cylinder, having the cavity 122 opened up and down in the middle thereof. Further, one of a top entrance and a bottom entrance opened in the cavity 122 of the gas collector 120 is used as an inhalation hole for the gas to be sensed, and the other one is used as an exhaust hole.

As shown in FIG. 4, the optical wave guider 130 includes optical waveguides OWG1~8 arranged to make light repetitively go zigzag in and out of the cavity 122. The optical waveguide refers to a device for transmitting light in a specific direction with the minimum loss based on total reflection, which basically includes a core portion having a high refractive index and a cladding portion having a low reflective index and surrounding the core. The optical waveguide may be materialized as one among a non-planer type, a planer type, a buried-channel type, a strip-loaded type, a ridge type, a rib type, and a diffused type, or by combination thereof them.

The optical wave guider 130 includes a first optical waveguide OWG1 that has a first entrance 123-1 to which light emitted from the light source 110 is incident, penetrates the wall 124 of the gas collector 120, and has a first exit 123-2 formed on an inner wall of the cavity 122 for an output to the cavity 122; a plurality of second optical waveguides OWG2~7 that make light exiting from the first exit 123-2 pass through the cavity 122, be incident to second entrances 126-1~126-6 formed on the inner wall, move within the wall 124 of the gas collector 120, and return to the cavity through second exits 127-1~127-6 formed in the inner wall; and a third optical waveguide OWG8 that has a third entrance 129-1 formed in the inner wall to make light exiting from the final second exit 127-6 among the second exits be incident thereto via the cavity 122, and a third exit 129-2 that penetrates the wall 124 of the gas collector 120 for an output to the outside.

The optical wave guider 130 includes the first optical waveguide OWG1 for transmitting light from an outer left side of the gas collector 120 to a starting point of a first optical path L1 via a topmost portion of the wall 124, a second optical waveguide-1 OWG2 guiding an input to an ending point of the first optical path L1, moving within the wall 124, and leading to a starting point of a second optical path L2; a second optical waveguide-2 OWG3 guiding an input to an ending point of the second optical path L2, moving within the wall 124, and leading to a starting point of a third optical path L3; a second optical waveguide-3 OWG4 guiding an input to an ending point of the third optical path L3, moving within the wall 124, and leading to a starting point of a fourth optical path L4; a second optical waveguide-4 OWG5 guiding an input to an ending point of the fourth optical path L4, moving within the wall 124, and leading to a starting point of a fifth optical path L5; a second optical waveguide-5 OWG6 guiding an input to an ending point of the fifth optical path L5, moving within the wall 124, and leading to a starting point of a sixth optical path L6; a second optical waveguide-6 OWG7 guiding an input to an ending point of the sixth optical path L6, moving within the wall 124, and leading to a starting point of a seventh optical path L7; and the third optical waveguide OWG8 guiding an input to an ending point of the seventh optical path L7 and leading to the outside via the wall 124. Here, a total length L of the optical path passing through the gas within the cavity 122 is the sum of the first path L1 from the first exit 123-2 to the second entrance 126-1, the second path L2 from the second exit 127-1 to the second entrance 126-2, the third path L3 from the second exit 127-2 to the second entrance 126-3, the fourth path L4 from the second exit 127-3 to the second entrance 126-4, the fifth path L5 from the second exit 127-4 to the second entrance 126-5, the sixth path L6 from the second exit 127-5 to the second entrance 126-6, the seventh path L7 from the second exit 127-6 to the third entrance 129-1. Like this, the optical path increases in such a manner that light emitted from the light source 110 repetitively goes in and out of the cavity 122 filled with gas, and it is thus possible to achieve miniaturization of the optical gas sensor 100. In particular, it is possible to accurately measure gas by making the optical path longer even under environments of a small space and low gas concentration. In FIG. 4, the second optical waveguides are designed as six optical waveguides-1~6 OWG2~7, but the number of second optical waveguides may be increased or decreased in consideration of the size or shape according to applied fields.

The optical detector 140 is configured to detect and convert an optical signal into an electric signal, and may generally include silicon, gallium arsenide, etc. As the optical detector 140, there are a detector using a pyroelectric effect of converting an incident infrared ray into voltage to be detected, a semiconductor optical detector using a carrier generated in a semiconductor by absorption of light, etc.

Although it is not separately illustrated and described, the present invention may further include an analysis device (or a computer) for analyzing the detected light. Based on the foregoing Lambert's law, the analysis device calculates concentration of gas based on the quantity of light measured by the optical detector 140. In other words, the analysis device may include a look-up table where concentration values of gas are tabulated corresponding to the wavelength and quantity of light detected by the optical detector 140, and analyzes a concentration value of gas based on the quantity of light detected in a light receiver. Further, the analysis device may have an expression for calculating concentration of gas based on the wavelength and quantity of light detected by the optical detector 140, and use the expression to analyze a concentration value of gas based on the wavelength and quantity of the detected light.

FIG. 4 is a cross-section view of showing a pattern of the optical wave guider 130 of the optical gas sensor 100 according to the first embodiment of the present invention. As shown therein, the light emitted from the light source 110 enters the first entrance 123-1 and goes into the cavity 122 through the first exit 123-2. The light passed through the cavity goes into the second entrance 126-1 and comes out to the cavity at the second exit 127-1, thereby entering the second entrance 126-2. Then, the light comes out to the cavity 122 at the second exit 127-2 and goes into the second entrance 126-3; comes out to the cavity 122 at the second exit 127-3 and goes into the second entrance 126-4; comes out to the cavity 122 at the second exit 127-4 and goes into the second entrance 126-5; comes out to the cavity 122 at the second exit 127-5 and goes into the second entrance 126-6; and comes out from the second exit 127-6, passes through the cavity, goes into the third entrance 129-1, and exits from the third exit 129-2 to the outside.

Figure 5:
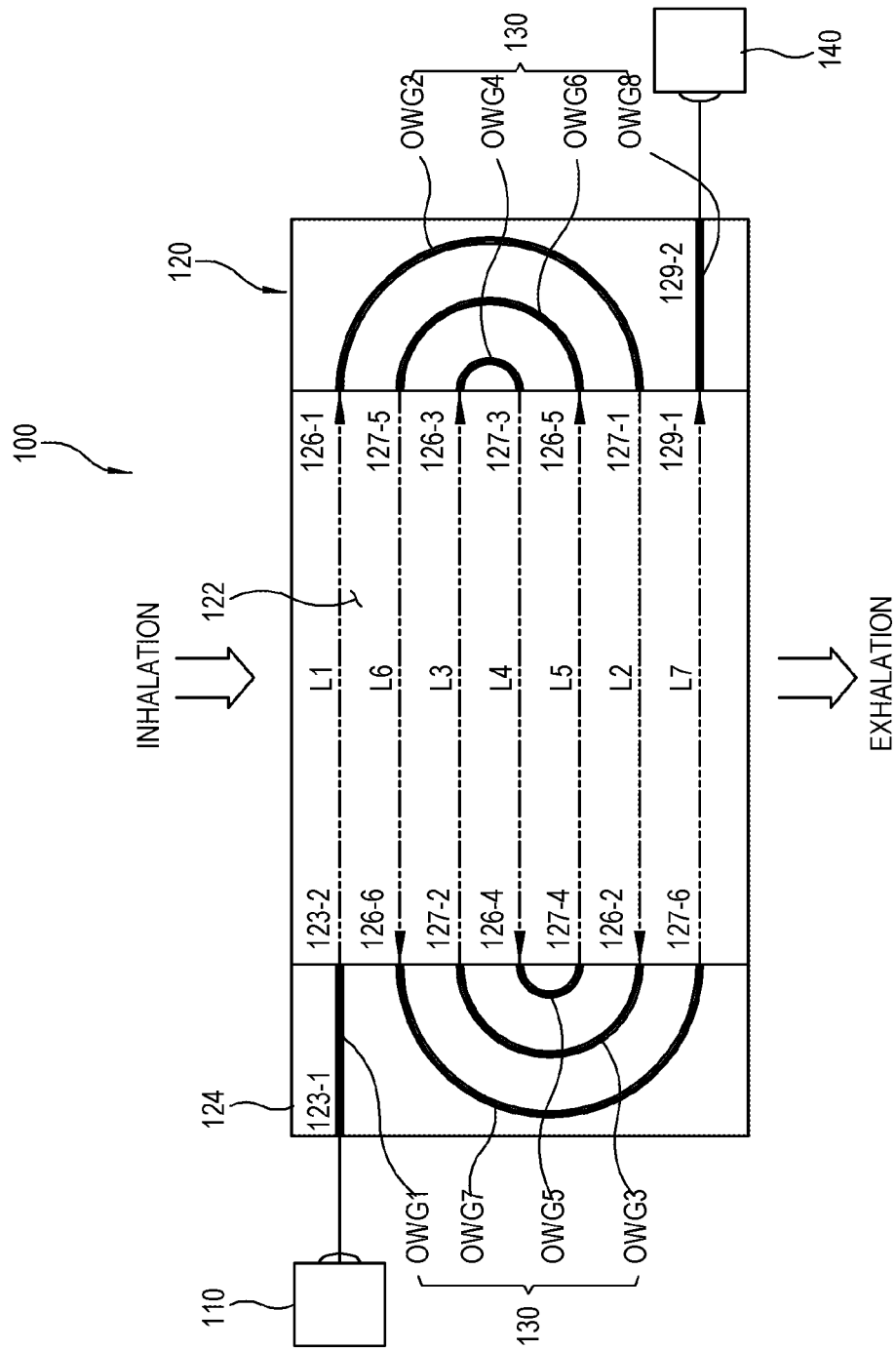
FIG. 5 is a cross-section view of an exit and an entrance of the optical gas sensor of FIG. 1.

FIG. 5 is a cross-section view of an optical gas sensor 100 according to a second embodiment of the present invention. As shown therein, the optical wave guider 130 includes a first optical waveguide OWG1 for transmitting light from an outer left side of the gas collector 120 to a starting point of a first optical path L1 of the cavity 122 via a topmost portion of the wall 124, a second optical waveguide-1 OWG2 guiding an input to an ending point of the first optical path L1, moving within the wall 124, and leading to a starting point of a sixth optical path L6; a second optical waveguide-2 OWG3 guiding an input to an ending point of the sixth optical path L6, moving within the wall 124, and leading to a starting point of a third optical path L3; a second optical waveguide-3 OWG4 guiding an input to an ending point of the third optical path L3, moving within the wall 124, and leading to a starting point of a fourth optical path L4; a second optical waveguide-4 OWG5 guiding an input to an ending point of the fourth optical path L4, moving within the wall 124, and leading to a starting point of a fifth optical path L5; a second optical waveguide-5 OWG6 guiding an input to an ending point of the fifth optical path L5, moving within the wall 124, and leading to a starting point of a second optical path L2; a second optical waveguide-6 OWG7 guiding an input to an ending point of the second optical path L2, moving within the wall 124, and leading to a starting point of a seventh optical path L7; and a third optical waveguide OWG8 guiding an input to an ending point of the seventh optical path L7 and leading to the outside via the wall 124.

The optical wave guider 130 according to the second embodiment can reduce an optical loss since the second optical waveguides-1, 2, 5, 6 OWG2~3 and 6~7 arranged within the wall 124 of the gas collector 120 have a greater curvature than that of the first embodiment except the second optical waveguides-2 and 3 OWG3~4.

Figure 6:
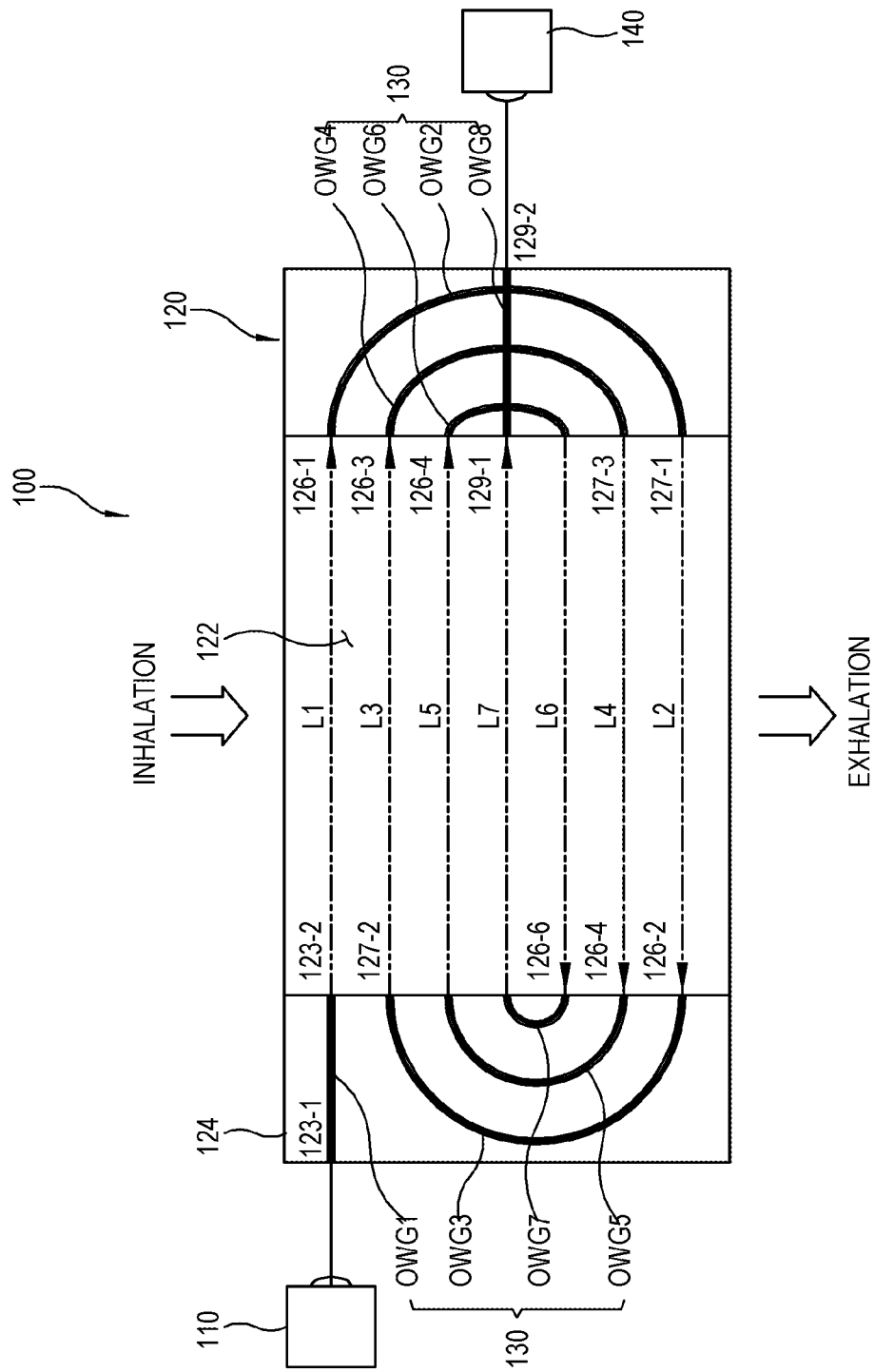
FIG. 6 is a cross-section view of an optical gas sensor according to a second embodiment of the present invention.

FIG. 6 is a cross-section view of an optical gas sensor 100 according to a third embodiment of the present invention. As shown therein, the optical wave guider 130 includes a first optical waveguide OWG1 for transmitting light from an outer left side of the gas collector 120 to a starting point of a first optical path L1 of the cavity 122 via a topmost portion of the wall 124, a second optical waveguide-1 OWG2 guiding an input to an ending point of the first optical path L1, moving within the wall 124, and leading to a starting point of a seventh optical path L7; a second optical waveguide-2 OWG3 guiding an input to an ending point of the seventh optical path L7, moving within the wall 124, and leading to a starting point of a second optical path L2; a second optical waveguide-3 OWG4 guiding an input to an ending point of the second optical path L2, moving within the wall 124, and leading to a starting point of a sixth optical path L6; a second optical waveguide-4 OWG5 guiding an input to an ending point of the sixth optical path L6, moving within the wall 124, and leading to a starting point of a third optical path L3; a second optical waveguide-5 OWG6 guiding an input to an ending point of the third optical path L3, moving within the wall 124, and leading to a starting point of a fifth optical path L5; a second optical waveguide-6 OWG7 guiding an input to an ending point of the fifth optical path L5, moving within the wall 124, and leading to a starting point of a fourth optical path L4; and a third optical waveguide OWG8 guiding an input to an ending point of the fourth optical path L4 and leading to the outside via the wall 124. In this case, the third optical waveguide OWG8 has to be not on the same plane as but formed above or below (with respect to the surface of the accompanying drawing) the second optical waveguide-1 OWG2, the second optical waveguide-3 OWG4, and the second optical waveguide-5 OWG6 so as to avoid an overlapping pathway.

The optical wave guider 130 according to the third embodiment can reduce an optical loss since the second optical waveguides-1~5 OWG2~6 arranged within the wall 124 of the gas collector 120 have a greater curvature than that of the first embodiment except the second optical waveguide-6 OWG7.

Figure 7:
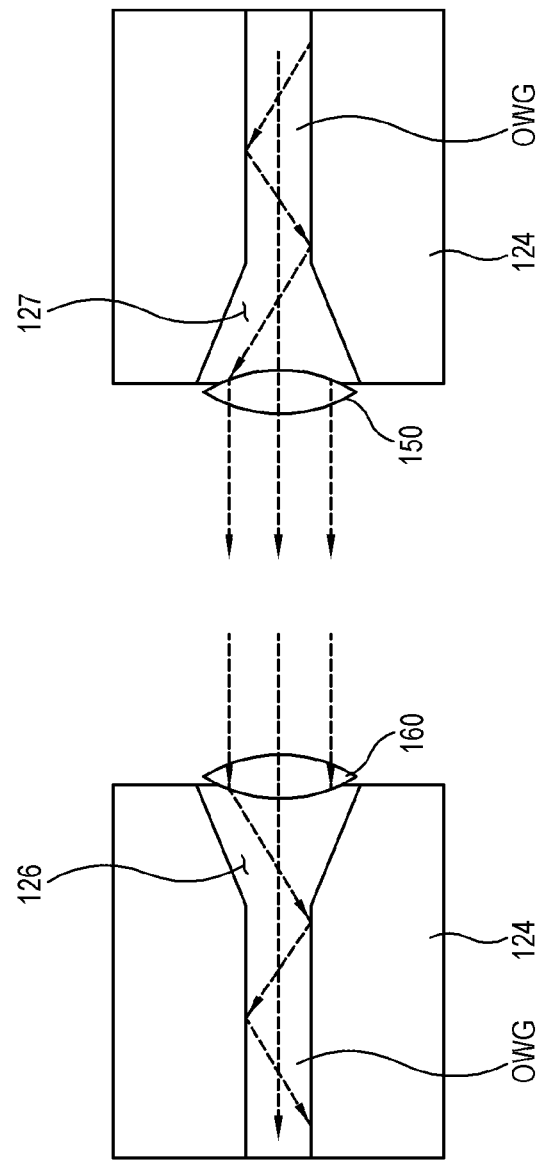
FIG. 7 is a cross-section view of an optical gas sensor according to a third embodiment of the present invention.

FIG. 7 illustrates shapes of an entrance 126 and an exit 127 in an optical wave guider OWG according to a fourth embodiment of the present invention. To transmit light from the exit 127 to the entrance 126 without any loss in the cavity, the exit 127 may be shaped like a funnel that becomes gradually wider, and the entrance 126 may be shaped like a funnel that becomes gradually narrower. Of course, the exit 127 and the entrance 126 may be shaped symmetrically or asymmetrically to each other, and may have an elliptical, polygonal or concave shape as well as a circular shape.

A lens refers to a device made by processing a surface of glass or the like material having high transmissivity of light to thereby focus or disperse light. To reduce the optical loss in the cavity, a collimating lens 150 is mounted to one end of the exit 127 and makes exiting light go parallel into the entrance without dispersing the exiting light, and a condensing lens 160 is mounted to one end of the entrance 126 and makes received light converge upon each optical waveguide. Here, the collimating lenses are lenses for making the light go parallel without dispersion, and the condensing lens are lenses for making the light converge. The exit 127 and the entrance 126 may employ optical antennas instead of the lenses. To have these effects, a single lens may be provided, or many lenses may be combined.

Figure 8:
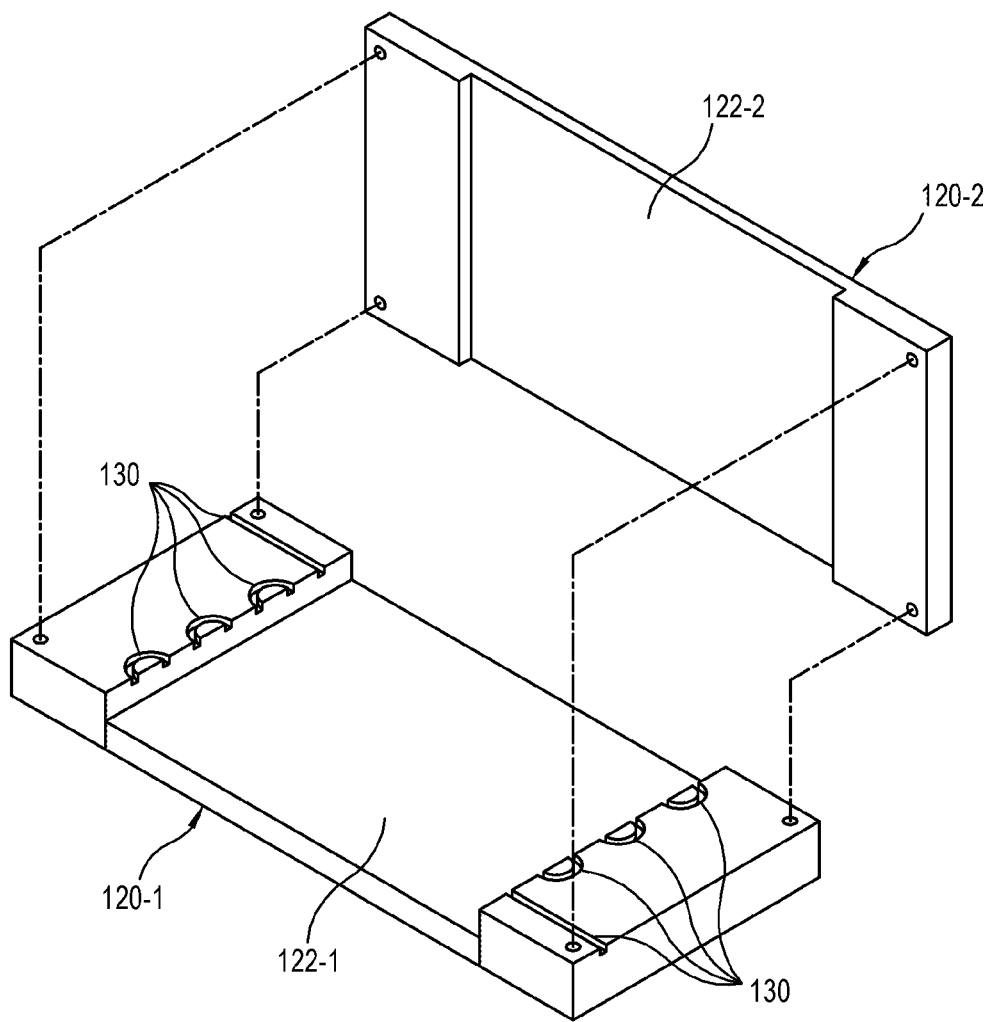
FIG. 8 is an exploded perspective view of the optical gas sensor of FIG. 3.

FIG. 8 is an exploded perspective view of the optical gas sensor of FIG. 3, in which two substrates, i.e. a first substrate 120-1 and a second substrate 120-2 are combined. As shown therein, the first substrate 120-1 is formed with a first cavity 122-1 shaped like a groove recessed on one surface thereof and collecting gas to be sensed, and an optical wave guider 130. The second substrate 120-2 is formed with a second cavity 122-2 corresponding to the first cavity 122-1 of the first substrate 120-1. In this case, the optical wave guider 130 provided as a groove recessed on the first substrate 120-1 may be used as it is, or an optical fiber 200 may be inserted in the optical wave guider 130.

Figure 9:
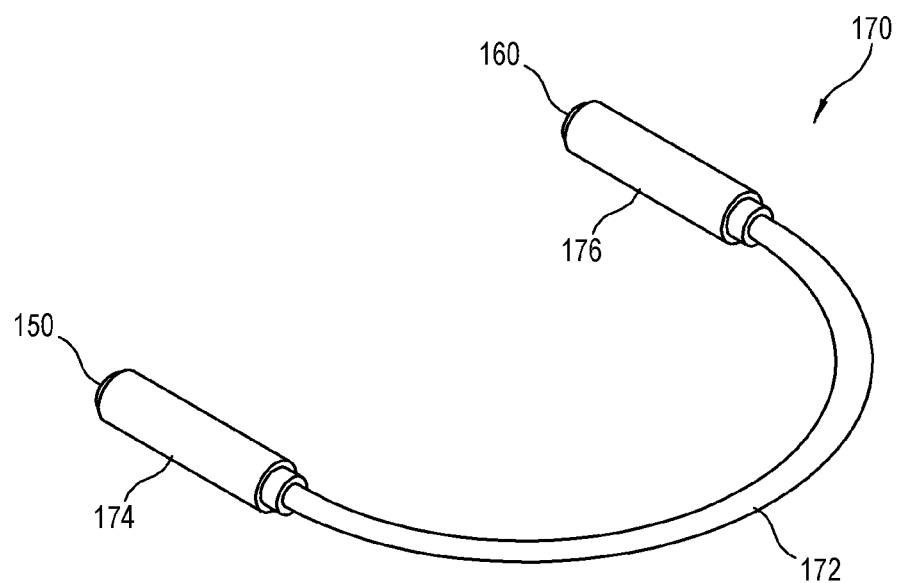
FIG. 9 shows an example of optical fiber used in an optical wave guider.

FIG. 9 illustrates an example of an optical fiber 200 used in the optical wave guider 130 used according to an embodiment of the present invention. As shown therein, when an optical fiber is used for the optical wave guider 130, opposite ends of each optical fiber 170 may be fabricated to have a proper shape for emitting and receiving light. For example, the optical fiber 170 includes a light transmitter 172, and the light transmitter 172 includes a first connecting portion 174 for connecting with the collimating lens 150 of FIG. 7 at one end thereof corresponding to the light exit, and a second connecting portion 176 for connecting with the condensing lens 160 of FIG. 7 at the other end thereof corresponding to the light entrance.

Figure 10:
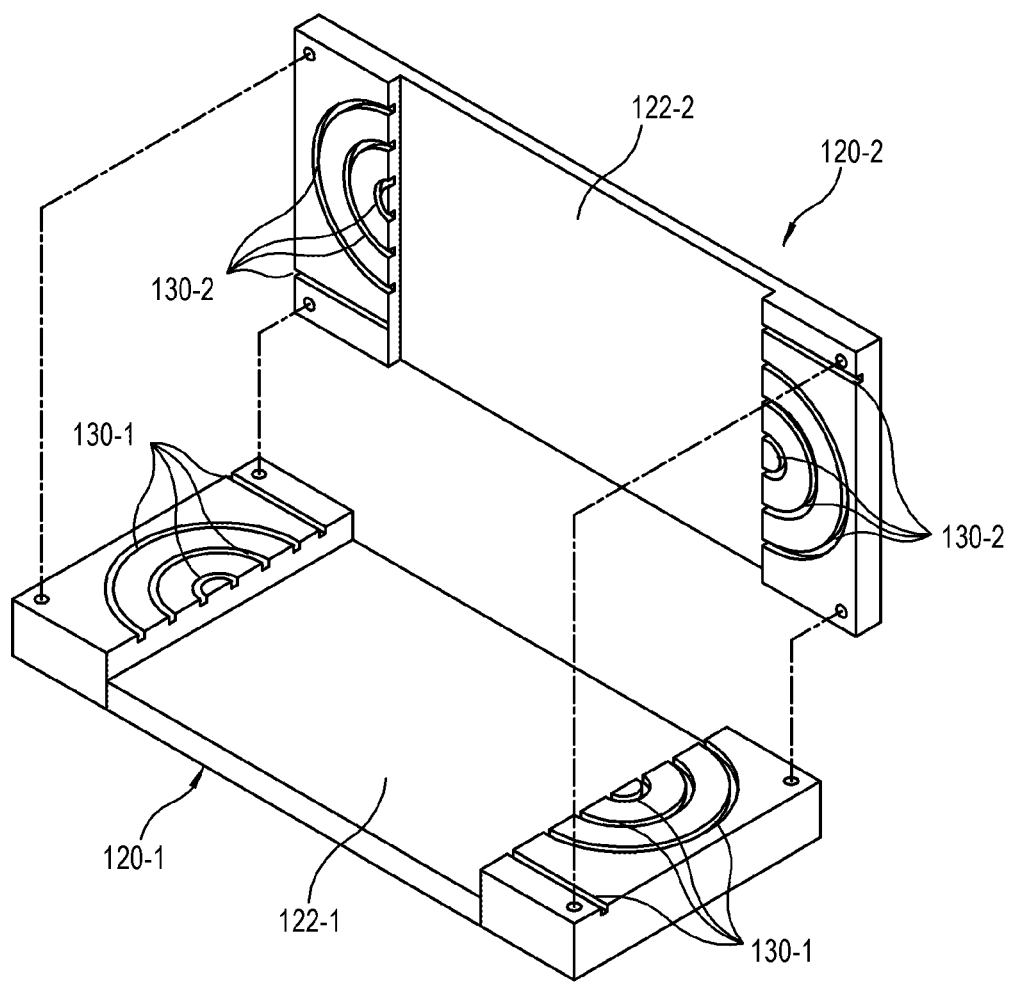
FIG. 10 is an exploded perspective view of an optical gas sensor according to a fourth embodiment of the present invention.

FIG. 10 is an exploded perspective view of an optical gas sensor 100 according to a fourth embodiment of the present invention, which includes two substrates. As shown therein, the first substrate 120-1 is formed with a first cavity 122-1 for collecting gas to be sensed on one surface thereof, and a groove recessed corresponding to an optical wave guider 130-1. The second substrate 120-2 is formed with a second cavity 122-2 and a second optical wave guider 130-2 which are symmetric with the first cavity 122-1 and the first optical wave guider 130-1 of the first substrate 120-1. According to the fourth embodiment, the first substrate 120-1 having the first cavity 122-1 and the first optical wave guider 130-1 and the second substrate 120-2 having the second cavity 122-2 and the second optical wave guider 130-2 are assembled into the optical gas sensor 100.

Figure 11:
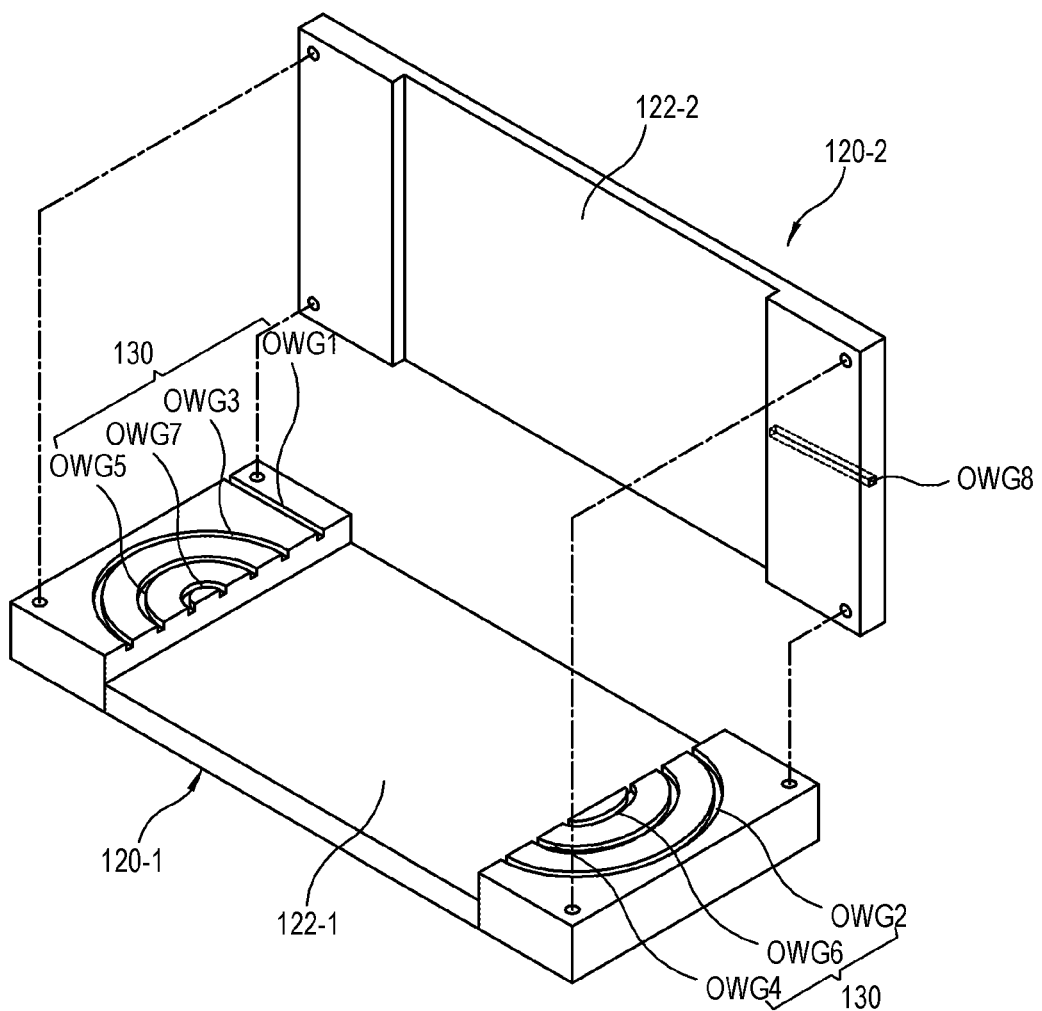
FIG. 11 is an exploded perspective view of an optical gas sensor according to a fifth embodiment of the present invention.

FIG. 11 is an exploded perspective view of an optical gas sensor 100 according to a fifth embodiment of the present invention, which includes two substrates. As shown therein, the first substrate 120-1 is formed with a first cavity 122-1 shaped like a groove recessed on one surface thereof and collecting gas to be sensed, and an optical wave guider 130-1. In this case, the first substrate 120-1 does not include the third optical waveguide OWG8 to avoid an overlapping pathway with the second optical waveguide-1 OWG2, the second optical waveguide-3 OWG4 and the second optical waveguide-5 OWG6. Instead, the third optical waveguide OWG8 is formed on an opposite face of the second substrate 120-2. Further, a second exit 127-6 of the second optical waveguide-6 OWG7 is designed to face toward a third entrance 129-1 of the third optical waveguide OWG8. Such an upward and downward arrangement may be more easily designed by using the optical fiber of FIG. 9.

Figure 12:
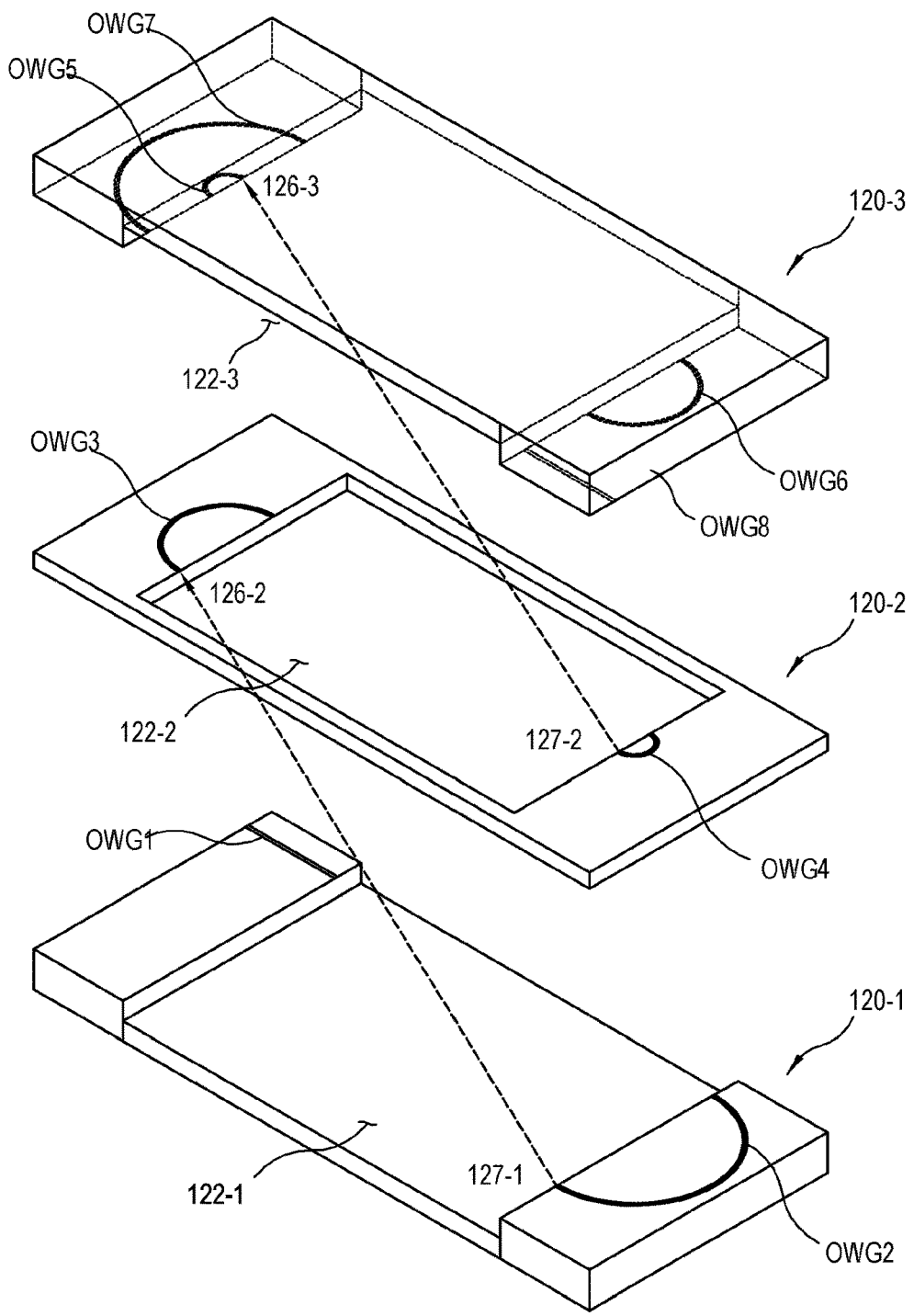
FIG. 12 is an exploded perspective view of an optical gas sensor according to a sixth embodiment of the present invention.

FIG. 12 is an exploded perspective view of an optical gas sensor 100 according to a sixth embodiment of the present invention, which includes three substrates 120-1, 120-2 and 120-3. As shown therein, a first substrate 120-1 includes a first cavity 122-1 for collecting gas to be sensed on one surface thereof, and grooves recessed corresponding to the first optical waveguide OWG1 and the second optical waveguide1 OWG2. A second substrate 120-2 includes a second cavity 122-2 for collecting gas to be sensed on one surface thereof, and grooves recessed corresponding to the second optical waveguide-2 OWG3 and the second optical waveguide-3 OWG4. In this case, a second exit 127-1 of the second optical waveguide-1 OWG2 formed in the first substrate 120-1 has to face toward a second entrance 126-2 of the second optical waveguide-2 OWG3 of the second substrate 120-2. A third substrate 120-3 includes a third cavity 122-3 for collecting gas to be sensed on one surface thereof, and grooves recessed corresponding to the second optical waveguide-4 OWG5, the second optical waveguide-5 OWG6, the second optical waveguide-6 OWG7 and the third optical waveguide OWG8. In this case, a second exit 127-2 of the second optical waveguide-3 OWG4 formed in the second substrate 120-2 has to face toward a second entrance 126-3 of the second optical waveguide-4 OWG5 of the third substrate 120-3. Such an upward and downward arrangement may be more easily designed by using the optical fiber of FIG. 9. The optical wave guiders OWG1~8 partially divisionally patterned on the first to third substrates are not limited to the pattern shown in FIG. 12, but may be variously patterned.

The optical gas sensor 100 shown in FIG. 8, FIG. 10, FIG. 11 and FIG. 12 is fabricated to include two or three substrates, but may include four or more substrates.

Figure 13:
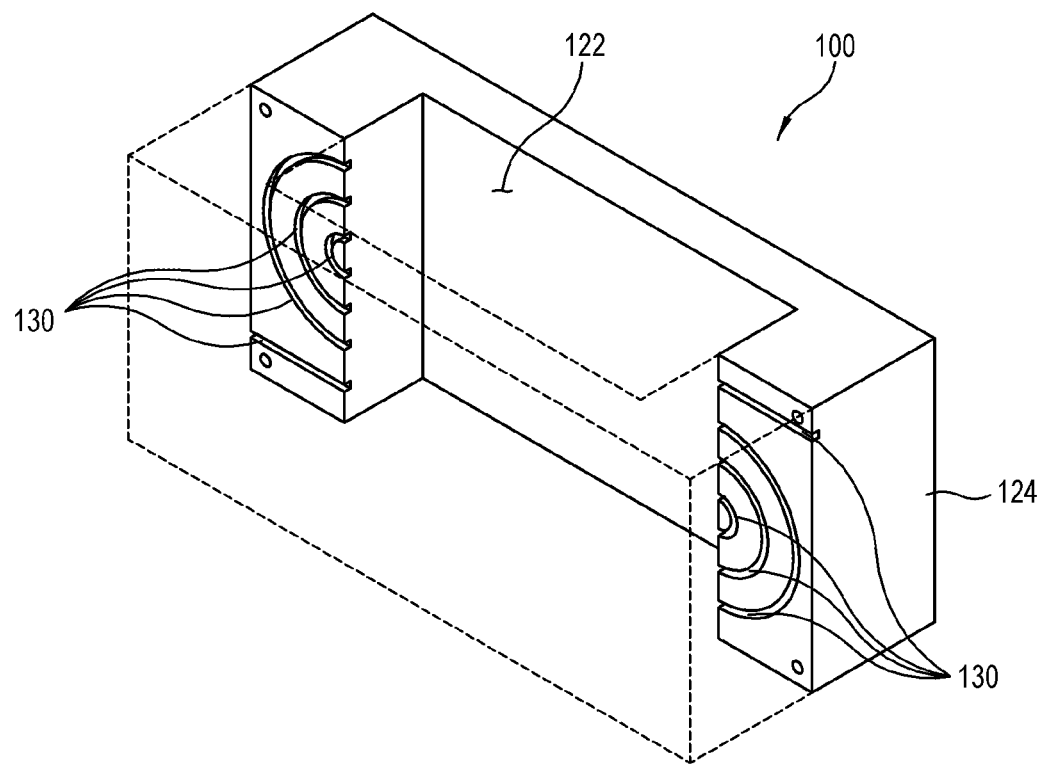
FIG. 13 is a perspective view of an optical gas sensor according to a seventh embodiment of the present invention.

FIG. 13 is a perspective view of an optical gas sensor according to a seventh embodiment of the present invention. The optical gas sensor 100 is shaped like a rectangular box, and the optical wave guider 130 is formed within a wall 124 of a rectangular box-shaped gas collector 120.

Figure 14:
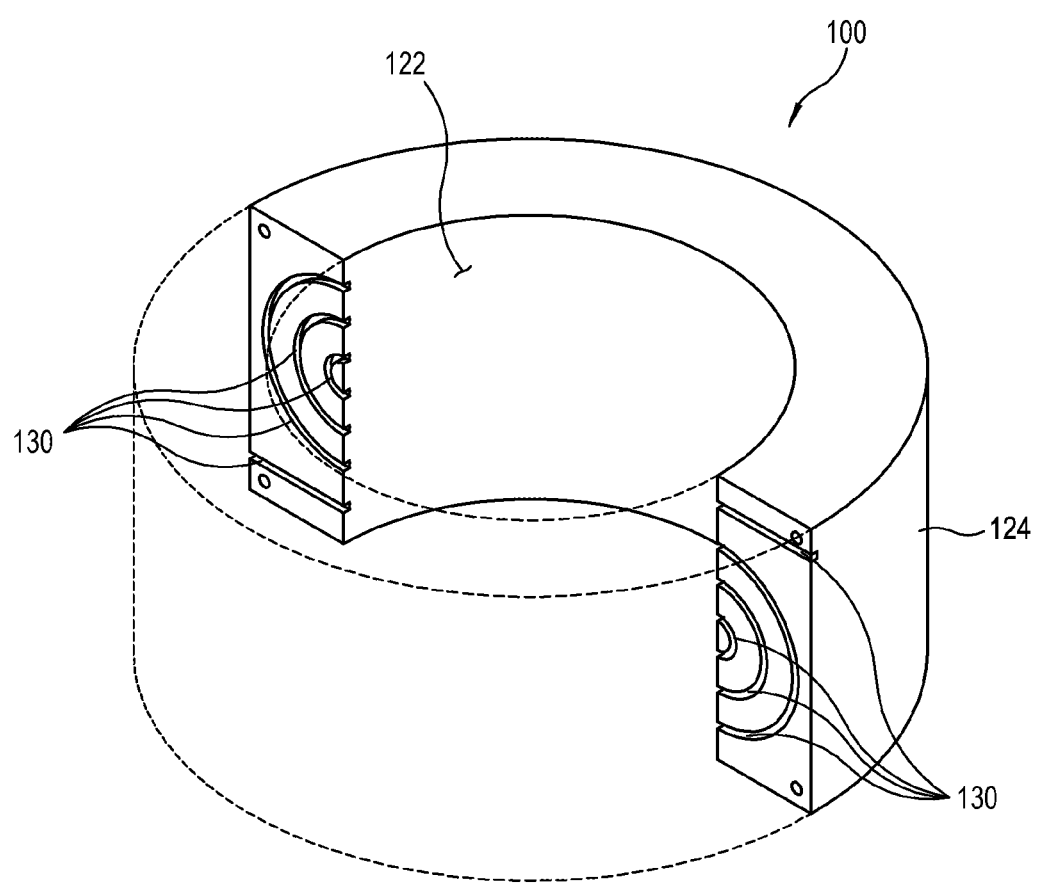
FIG. 14 is a perspective view of an optical gas sensor according to an eighth embodiment of the present invention.

FIG. 14 is a perspective view of an optical gas sensor according to an eighth embodiment of the present invention. An optical gas sensor 100 has a cylindrical shape, and an optical wave guider 130 is formed within a wall 124 of a cylindrical gas collector 120.

The optical gas sensors 100 shown in FIGS. 13 and 14 are shaped like a box and a cylinder, respectively. Alternatively, the optical gas sensor may be shaped like an elliptical barrel, a polygonal barrel, an amorphous barrel, and the like barrel.

Figure 15:
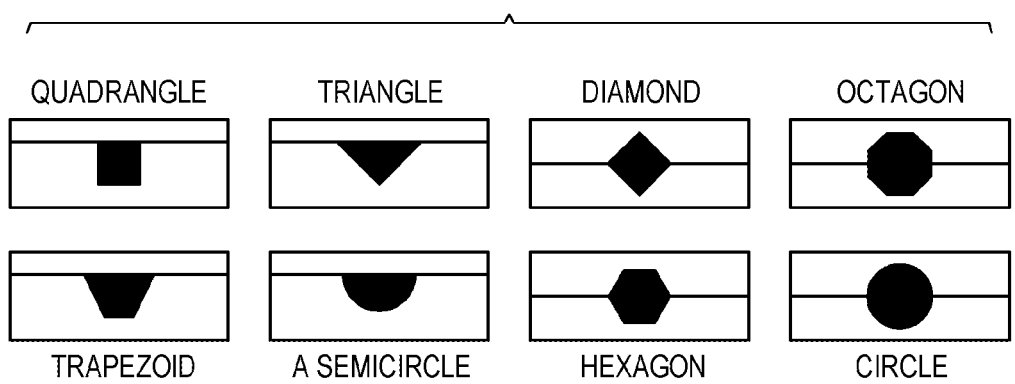
FIG. 15 is a cross-section view of an optical waveguide.

FIG. 15 is a cross-section view of various optical wave guides 130 in an optical gas sensor 100 according to embodiments of the present invention. The cross-section of the optical waveguide 130 may be shaped like one of a quadrangle, a trapezoid, a hexagon, a triangle, a semicircle, a circle, a diamond, and an octagon.

Figure 16:
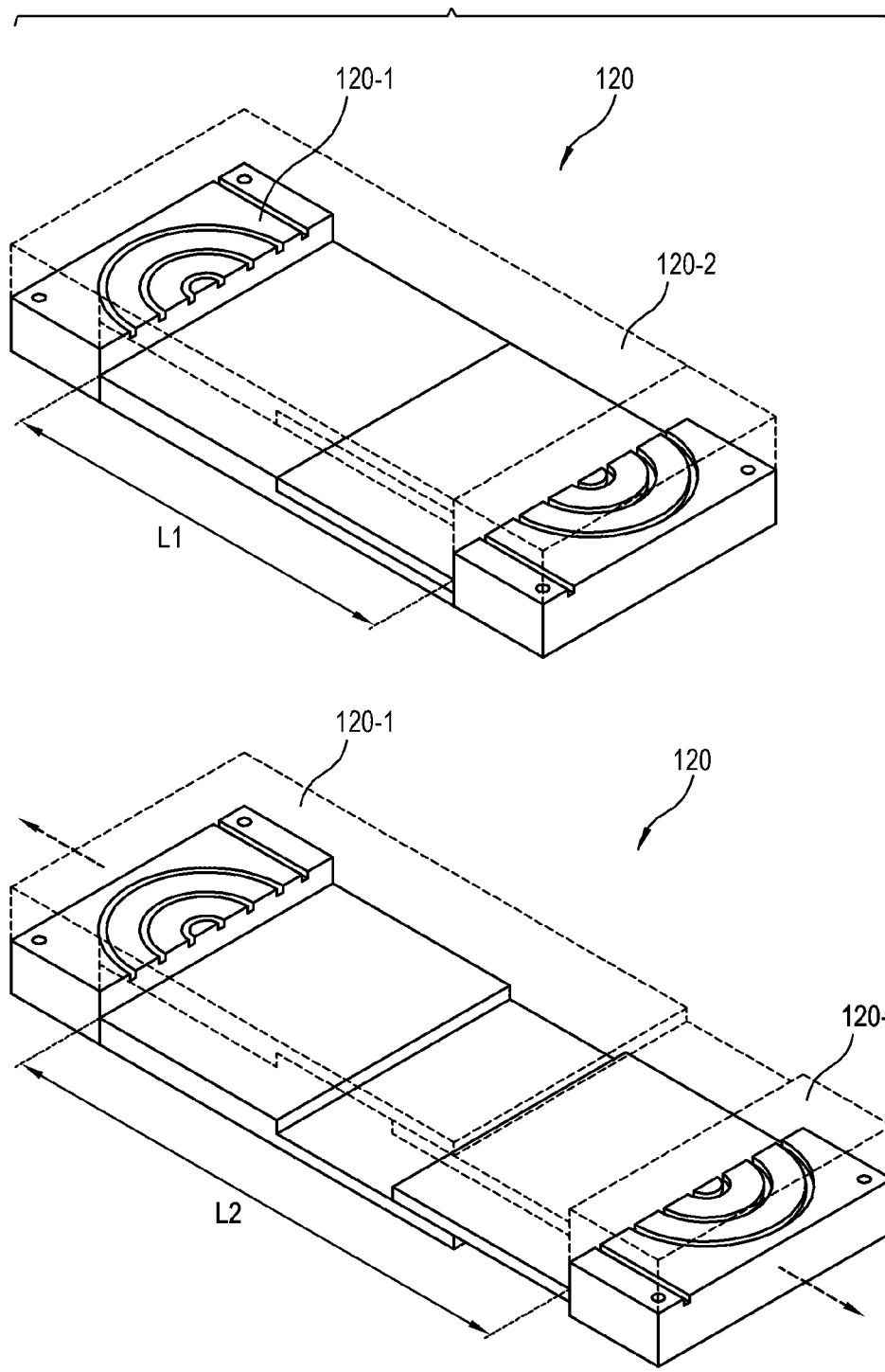
FIG. 16 is a perspective view of an optical gas sensor according to a ninth embodiment of the present invention.

FIG. 16 is a perspective view of an optical gas sensor 100 according to a ninth embodiment of the present invention, which shows an example that an optical path is adjustable between L1 and L2. The gas collector 120 includes a first gas collector 120-1 and a second gas collector 120-2 which are slidably movable and coupled to each other. Of courses, there may be various examples of making the optical path adjustable besides the example shown in the embodiment of FIG. 15. When gas to be sensed has low concentration, the optical path is extended to L2. When the optical path is extended, intensity of light may be increased.

Figure 17:
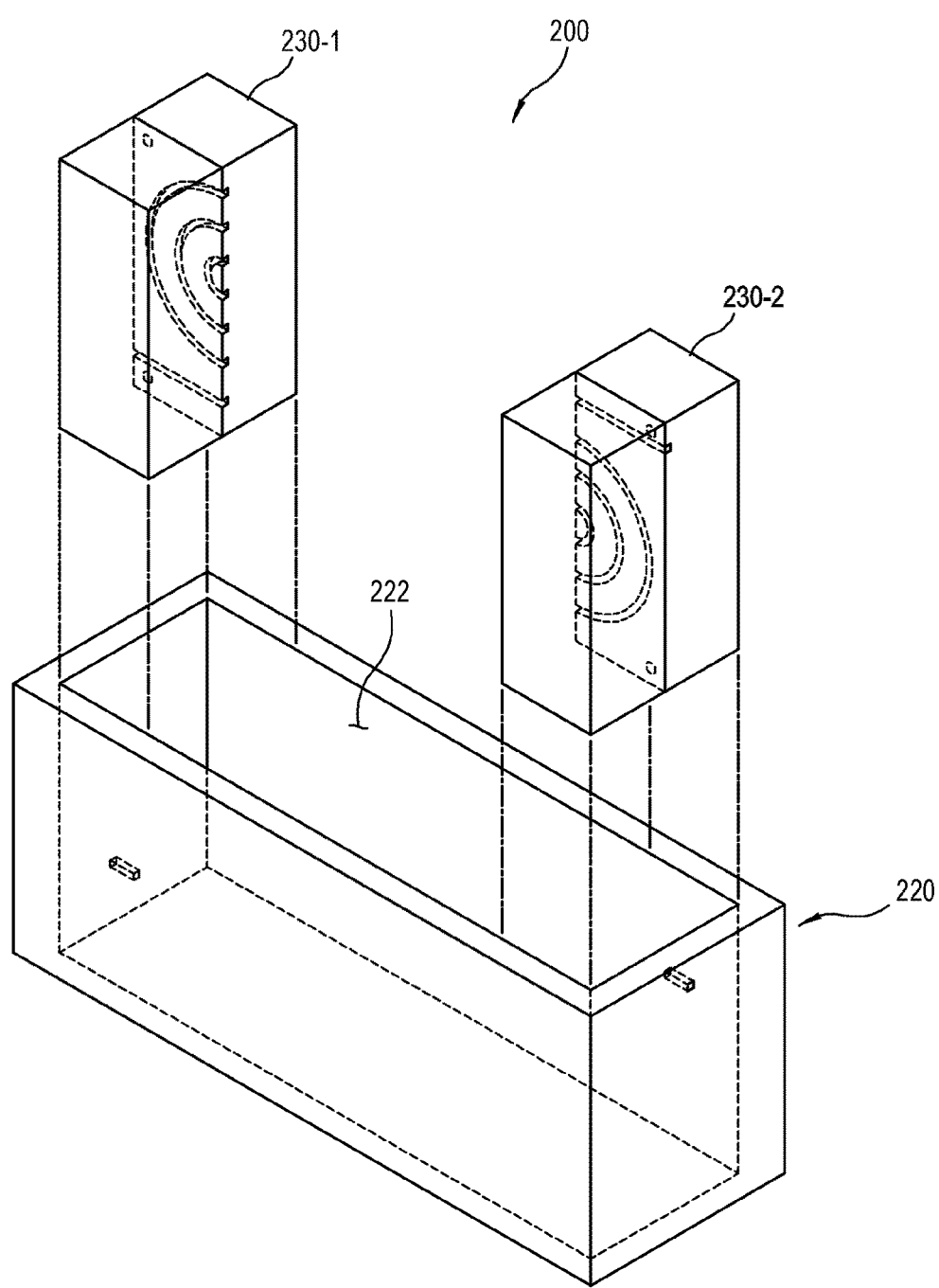
FIG. 17 is an exploded perspective view of an optical gas sensor according to a tenth embodiment of the present invention.

FIG. 17 is a perspective view of an optical gas sensor 200 according to a tenth embodiment of the present invention, which includes first and second optical wave guiders 230-1 and 230-2 fabricated separately from a gas collector 220 having a cavity 222 for collecting gas. As shown in FIG. 17, the gas collector 220 is shaped like a rectangular box to be filled with gas at the center thereof, but there are no limits to the shape of the rectangular box. The first and second optical wave guiders 230-1 and 230-2 are coupled to the cavity of the gas collector 220, leaving a predetermined distance therebetween. Thus, the gas collector 220 and the optical wave guiders 230-1 and 230-2 are not integrally but separately fabricated and then coupled to each other.

The optical gas sensor according to the present invention may be used for sensing air pollution, sensing respiratory gas for medical examination, or sensing gas under a specific environment such as inside a manhole, etc. As diseases diagnosed based on a human-body respiratory gas sensed by the optical gas sensor, there are a chronic pulmonary disease, asthma, chronic cough, bronchiectasis, pulmonary tuberculosis, lung cancer, thyroid cancer, apnea (asphyxia), a kidney disease, diabetes, smoking, drinking, etc.

The optical gas sensor according to the present invention may be provided as a laptop type, or mounted to or manufactured integrally with a mask, a cellular phone, a phone accessory, a nipple, a straw, a headphone, a Bluetooth earphone, a necklace, smart glasses, a pen for a smart phone, etc.

Although the present invention has been described with the limited and exemplary embodiments and drawings, the present invention is not limited to the foregoing exemplary embodiments, and various changes and modifications can be made from these descriptions by a person having an ordinary skilled in the art to which the present invention pertains.

Therefore, the scope of the invention has to be defined in the appended claims and their equivalents without limitations to the described exemplary embodiments.

INDUSTRIAL APPLICABILITY

The optical gas sensor according to the embodiments of the present invention may be employed as a diagnosis device for diagnosing health conditions of a human body.

The invention claimed is:
1. An optical gas sensor comprising:
    a light source which emits light;
    a gas collector which comprises a wall and forms a cavity to be filled with gas to be sensed;
    an optical wave guider which is formed in the wall along a curved path and guides light, which is emitted from the light source, to be transmitted from the cavity to the wall and redirected to the cavity after passing through the wall; and an optical detector which detects the light in the gas collector.

2. An optical gas sensor comprising:
a light source which emits light;
a gas collector which comprises a cavity configured to be filled with gas to be sensed;
an optical wave guider which guides light emitted from the light source to be output to the cavity, and guides the output light to be output again to the cavity after passing through the cavity of the gas collector; and
an optical detector which detects light output from the optical wave guider,
wherein the optical wave guider comprises:
an optical inlet which comprises an entrance to which light emitted from the light source is input, and an exit from which the light input through the entrance is output to the cavity;
at least one optical bypass by which light passed through the cavity is bypassed to be output again to the cavity; and
an optical outlet which outputs light passed through the optical bypass to an outside.

3. The optical gas sensor according to claim 1, wherein the gas collector is shaped like a barrel opened up and down.

4. The optical gas sensor according to claim 1, wherein the gas collector is shaped like a cylinder or a rectangular box.

5. The optical gas sensor according to claim 1, wherein the optical wave guider is formed on face-to-face surfaces of two or more substrates.

6. The optical gas sensor according to claim 1, wherein the optical wave guider is formed on one surface of face-to-face surfaces of two or more substrates.

7. The optical gas sensor according to claim 2, wherein the gas collector comprises two substrates, and
the optical inlet and the optical bypass are formed in one substrate, and the optical outlet is formed in the other adjacent substrate.

8. The optical gas sensor according to claim 1, wherein the gas collector comprises three substrates, and
the optical wave guider is formed in a middle substrate among the three substrates.

9. The optical gas sensor according to claim 2, wherein the gas collector comprises three or more substrates, and
the optical inlet, the optical bypass and the optical outlet are dispersedly formed throughout the three or more substrates.

10. The optical gas sensor according to claim 1, wherein the optical wave guider has a cross section shaped like one of a quadrangle, a trapezoid, a hexagon, a triangle, a semicircle, a circle, a diamond and an octagon.

11. The optical gas sensor according to claim 1, wherein the optical wave guider comprises an optical entrance for an input to the cavity and an optical exit for an output from the cavity, and at least one of the optical entrance or the optical exit is shaped like a funnel.

12. The optical gas sensor according to claim 11, wherein the optical exit comprises a collimating lens.

13. The optical gas sensor according to claim 11, wherein the optical entrance comprises a condensing lens.

14. The optical gas sensor according to claim 1, wherein a distance between an optical entrance for an input to the cavity and an optical exit for an output from the cavity is adjustable.

15. The optical gas sensor according to claim 14, wherein a quantity of light emitted from the light source is varied depending on adjustment of the distance.

16. The optical gas sensor according to claim 1, further comprising a second optical wave guider that guides the light, which is redirected to the cavity after passing through the wall, along a second curved path to be redirected to the cavity again after passing through the wall,
wherein the optical wave guider is disposed on a first side of the wall, and the second optical wave guider is disposed on a second side of the wall, opposite to the first side.

17. The optical gas sensor according to claim 1, wherein the optical wave guider is formed by a plurality of grooves disposed on at least one substrate.

18. The optical gas sensor according to claim 1, wherein the optical wave guider is formed by an optical fiber.

* * * * *